United States Patent
Caciula et al.

(10) Patent No.: US 9,902,669 B2
(45) Date of Patent: Feb. 27, 2018

(54) OXIDATIVE DEHYDROGENATION PROCESS WITH HYDROCARBON MODERATOR GAS AND REDUCED NITROGEN FEED

(71) Applicant: TPC Group LLC, Houston, TX (US)

(72) Inventors: Liana Caciula, Houston, TX (US); Clifford A. Maat, Pearland, TX (US); Mark P. Kaminsky, Friendswood, TX (US); Michael O. Nutt, Pearland, TX (US); Jillian M. Horn, Houston, TX (US); Joseph G. Duff, League City, TX (US)

(73) Assignee: TPC GROUP LLC, Houston, TX (US)

( * ) Notice: Subject to any disclaimer, the term of this patent is extended or adjusted under 35 U.S.C. 154(b) by 288 days.

(21) Appl. No.: 14/771,227

(22) PCT Filed: Mar. 7, 2014

(86) PCT No.: PCT/US2014/021481
§ 371 (c)(1),
(2) Date: Aug. 28, 2015

(87) PCT Pub. No.: WO2014/138510
PCT Pub. Date: Sep. 12, 2014

(65) Prior Publication Data
US 2016/0002126 A1  Jan. 7, 2016

Related U.S. Application Data

(60) Provisional application No. 61/774,370, filed on Mar. 7, 2013, provisional application No. 61/844,483, filed on Jul. 10, 2013.

(51) Int. Cl.
C07C 5/48 (2006.01)
C07C 2/10 (2006.01)
C07C 2/32 (2006.01)

(52) U.S. Cl.
CPC ............. *C07C 5/48* (2013.01); *C07C 2/10* (2013.01); *C07C 2/32* (2013.01); *B01J 2219/00006* (2013.01); *C07C 2523/745* (2013.01); *C07C 2531/14* (2013.01); *C07C 2531/22* (2013.01); *C07C 2531/24* (2013.01); *C07C 2531/30* (2013.01)

(58) Field of Classification Search
CPC .. C07C 5/48; C07C 2/10; C07C 11/08; C07C 11/167; C07C 2523/745; C07C 2531/14; C07C 2531/22; C07C 2531/24; C07C 2531/30; C07C 2/32; B01J 2219/00006
See application file for complete search history.

(56) References Cited

U.S. PATENT DOCUMENTS

| | | |
|---|---|---|
| 3,327,001 A | 6/1967 | Tschopp et al. |
| 3,341,620 A | 9/1967 | Clark et al. |
| 3,728,415 A | 4/1973 | Arganbright |
| 3,911,042 A | 10/1975 | Belov et al. |
| 3,925,498 A | 12/1975 | Stadig |
| 3,969,429 A | 7/1976 | Belov et al. |
| 4,083,844 A | 4/1978 | Gottschlich et al. |
| 4,595,788 A | 6/1986 | Yamamoto et al. |
| 5,162,595 A | 11/1992 | Wu |
| 5,405,817 A * | 4/1995 | Kuo ............ B01J 31/0212 502/113 |
| 5,653,916 A | 8/1997 | Disselhorst et al. |
| 7,417,173 B2 | 8/2008 | Crone et al. |
| 7,435,860 B2 | 10/2008 | Crone et al. |
| 7,488,857 B2 | 2/2009 | Johann et al. |
| 8,088,962 B2 | 1/2012 | Klanner et al. |
| 2008/0097133 A1 | 4/2008 | Crone et al. |
| 2010/0099936 A1 | 4/2010 | Shin et al. |
| 2011/0245568 A1 | 10/2011 | Khabashesku et al. |
| 2011/0288308 A1 | 11/2011 | Grasset et al. |
| 2014/0088332 A1* | 3/2014 | Rolland ................ C07C 5/48 585/326 |
| 2014/0163290 A1* | 6/2014 | Grune .................. C07C 5/48 585/626 |

FOREIGN PATENT DOCUMENTS

JP 2011148720 A 8/2011

OTHER PUBLICATIONS

Seyed Hamed Mahdaviani et al., "Selective ethylene dimerization toward 1-butene by a new highly efficient catalyst system and determination of its optimum operating conditions in a Buchi reactor", International Journal of Chemical Engineering and Applications, Oct. 2010, pp. 276-281, vol. 1, No. 3.

John S. Sterrett et al., "Kinetics of the oxidative dehydrogenation of butene to butadiene over a ferrite catalyst", Industrial & Engineering Chemistry Process Design and Development, 1974, pp. 54-59, vol. 13, No. 1.

L. Marshall Welch et al., "Butadiene via oxidative dehydrogenation", Hydrocarbon Processing, Nov. 1978, pp. 131-136.

* cited by examiner

Primary Examiner — Sharon Pregler
(74) Attorney, Agent, or Firm — Michael W. Ferrell

(57) ABSTRACT

Oxidative dehydrogenation includes: (a) providing a gaseous feed stream to a catalytic reactor, the feed stream comprising a dehydrogenation reactant, oxygen, superheated steam, hydrocarbon moderator gas and optionally nitrogen, wherein the molar ratio of moderator gas to oxygen in feed stream is typically from 4:1 to 1:1 and the molar ratio of oxygen to nitrogen in the feed stream is at least 2; (b) oxidatively dehydrogenating the reactant in the reactor to provide a dehydrogenated product enriched effluent product stream; and (c) recovering dehydrogenated product from the effluent product stream. One preferred embodiment is a process for making butadiene including dimerizing ethylene to n-butene in a homogeneous reaction medium to provide a hydrocarbonaceous n-butene rich feed stream and oxidatively dehydrogenating the n-butene so formed.

22 Claims, 5 Drawing Sheets

OXIDATIVE DEHYDROGENATION PROCESS WITH HYDROCARBON MODERATOR GAS AND REDUCED NITROGEN FEED

CLAIM FOR PRIORITY

This application is based upon PCT Application Serial No. PCT/US2014/021481, filed Mar. 7, 2014. Application No. PCT/US2014/021481 was based upon U.S. Provisional Application No. 61/774,370, filed Mar. 7, 2013, entitled "Oxidative Dehydrogenation Process With Hydrocarbon Moderator Gas and Reduced Nitrogen Feed" and was also based upon U.S. Provisional Application No. 61/844,483, filed Jul. 10, 2013, entitled "Manufacture of Butadiene from Ethylene With Hydrocarbon Moderator Gas and Reduced Nitrogen Feed". The priorities of the foregoing applications are hereby claimed and their disclosures incorporated herein by reference.

TECHNICAL FIELD

The present invention is directed to a process for producing dehydrogenated products by oxidative dehydrogenation in the presence of oxygen with a hydrocarbon moderator gas provided in the feed to the reactor. Typically, the process is characterized by reduced levels of nitrogen in the feed as compared with air-fed processes. A preferred embodiment produces butadiene from ethylene by dimerizing the ethylene followed by oxidative dehydrogenation.

BACKGROUND

Existing oxidative dehydrogenation processes can be relatively impurity-sensitive and energy intensive due to the large recirculation rates of steam and nitrogen employed.

In conventional processes, air is used as the oxygen source for the reaction because, in part, nitrogen in the air acts as a diluent to moderate the intense exotherm of the reaction in order to control temperatures. Process details are discussed at some length in Welch et al., *Butadiene via oxidative dehydrogenation*, Hydrocarbon Processing, November 1978, pp. 131-136. The article notes that molecular oxygen, air, or mixtures of air and oxygen, can be used as the oxygen source, p. 131, and notes that certain impurities in the feed, such as isobutylene, reduces yields per pass (p. 136).

Sources of oxygen other than air for oxidative dehydrogenation to make butadiene are also discussed in the following references.

U.S. Pat. No. 3,327,001 to Tschopp discloses by implication that oxygen sources other than air may be used in an oxidative dehydrogenation butadiene process. See Col. 2, last paragraph which continues to Col. 3. U.S. Pat. No. 7,417,173, to Crone et al., has similar disclosure at Col. 7, lines 22-44. See, also, US 2008/0097133, of Crone et al., at paragraphs, [0050], [0051] and U.S. Pat. No. 7,435,860, to Crone et al., Col. 7, lines 12-35.

U.S. Pat. No. 8,088,962, to Klanner et al., discusses oxygen content of feed to oxidative dehydrogenation as including molecular oxygen and various diluents including optionally saturated hydrocarbons at Col. 18, lines 27-34. No examples of using oxygen or a saturated hydrocarbon diluent in an oxydehydrogenation unit are provided in this reference.

Although the use of pure oxygen in dehydrogenation processes for making butadiene has been suggested, in practice, air has been used as the oxygen source for cost reasons and because nitrogen present from the air-fed process operates to moderate temperature in processes for industrial production. Large scale processes require purification and recycle. Nitrogen present, a non-condensable gas in the process, contributes substantially to operating costs.

In a traditional version of the oxidative dehydrogenation process, an excess flow of steam to n-butene molar ratio of 12:1 is used to control the exotherm. The temperature of the reactor feed also needs to be increased to around 750° F. The air flow to the reactor is carefully controlled to promote butadiene selectivity, while ensuring that little or no oxygen passes beyond the reactors. Suitably, the air flow is measured and oxygen feed is calculated. Flow is then adjusted so that the amount of oxygen present falls within optimal range for reaction selectivity.

Nitrogen acts as diluent for the hydrocarbon-rich reactor contents. It absorbs part of the heat of reaction thus helping control the exotherm as the reaction proceeds. It also prevents the formation of a flammable hydrocarbon/oxygen mixture in the event of a process upset that "kills" the oxidation reaction.

Unlike steam, which can be removed from the reactor effluent early in the process via condensation in the quenching section, nitrogen is not condensable at normal process conditions. It remains part of the product stream as this stream moves through compression, scrubbing, and absorption sections, and it drives the equipment size, the piping size, as well as the overall design considerations. The nitrogen content increases significantly from 15 wt % (reactor outlet), to 45 wt % (gas compressor outlet), to 47 wt % (scrubber O/H), to 85 wt % (absorber O/H) in a typical air-fed process.

This high 85 wt % nitrogen content of the absorber O/H correlates with a low heating value for the stream (~400 BTU/LB) and makes it unacceptable as boiler feed.

N-butene raw material for making butadiene is oftentimes scarce and difficult to obtain at prices suitable for commercial manufacturing operations. It is known in the art to dimerize ethylene to butene and use the recovered butene for manufacturing butadiene. U.S. Pat. No. 3,728,415 to Arganbright discloses producing butenes by dimerizing ethylene with a catalyst including palladium oxide with molybdenum oxide or tungsten oxide and using the product for dehydrogenation to make butadiene.

Other references of general interest include the following: U.S. Pat. Nos. 3,911,042 and 3,969,429 to Belov et al. which disclose titanium/aluminum catalyzed dimerization of ethylene and note the product is useful for making butadiene; U.S. Pat. No. 7,488,857 to Johann et al. which discloses coproduction of butadiene and butene-1 from butane; and United States Patent Application Publication No. US 2011/0288308 to Grasset et al. which discloses ethylene dimerization with titanium/aluminum catalyst.

It is proposed in Japanese Patent Publication 2011-148720 to manufacture butadiene from ethylene by way of dimerizing ethylene followed by oxidative dehydrogenation using specified catalysts to minimize impact of various impurities. The method proposed includes the following steps (I) and (II): a step (I) for producing n-butene essentially free of isobutene by dimerizing ethylene at a reaction temperature of 150 to 400° C. in the presence of a catalyst consisting of nickel, alumina, and silica having a nickel content of 0.0001 to 1 wt. %; and a step (II) for producing butadiene by performing an oxidative dehydrogenation reaction on the n-butene obtained in said step (I) with oxygen at a reaction temperature of 300 to 600° C. in the presence of a complex metal oxide comprising molybdenum and bismuth as essential ingredients.

SUMMARY OF INVENTION

There is provided in accordance with the invention an improved process for making butadiene including providing a hydrocarbonaceous n-butene rich stream; feeding the n-butene, oxygen and steam to an oxidative dehydrogenation reactor along with a hydrocarbon moderator gas. The improved process suitably includes a gas-phase, adiabatic, partial oxidation of n-butene(s) to form butadiene, wherein the feed stream is enriched in oxygen and hydrocarbon gas injection into the reactor feed supplements the "heat sink" effect lost by removal of nitrogen.

Preferably nitrogen concentration in the feed is reduced as compared with air-fed processes such that the $O_2/N_2$ ratio in the feed is larger than that of air. A hydrocarbon moderator gas may be selected from: methane, ethane, propane, butane, pentane, hexane or mixtures of two or more of these gasses. A particularly preferred moderator gas is methane which may be fed to the reactor as natural gas.

In some embodiments a moderator gas such as methane can be used in place of steam, with moderator gas: reactant hydrocarbon molar ratios of anywhere from 0.5:1 to 15:1, if so desired, such that the moderator gas:oxygen molar ratios in the feed are quite high, up to about 50 or so.

The inventive process may utilize an ethylene raw material feed wherein the ethylene is dimerized to n-butene in a homogeneous reaction medium prior to oxidative dehydrogenation.

In another embodiment, there is provided a process for co-producing butadiene and butene-1 from ethylene.

The invention enables reduced equipment size and additional options for product recovery and reduces both utility costs and capital costs as described hereinafter. A further advantage is that gas removed from the process has a much higher heating value than gas removed from an air-fed process which facilitates heat recovery.

BRIEF DESCRIPTION OF DRAWINGS

The invention is described in detail below with reference to the drawings wherein like numerals designate similar parts and wherein.

DETAILED DESCRIPTION

Figure 1:
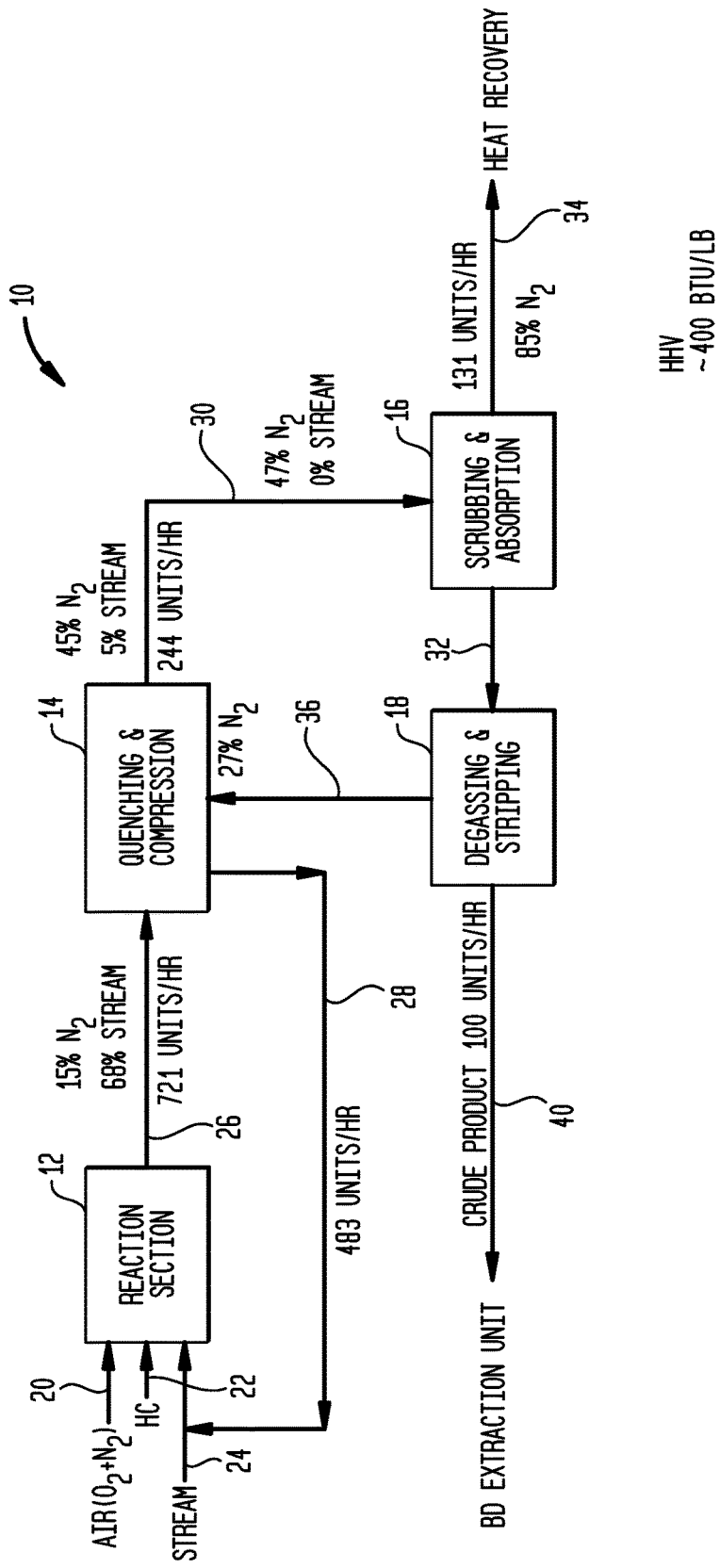
FIG. 1 is a schematic diagram illustrating an oxidative dehydrogenation system to make butadiene from butene with air as the oxygen source.

The invention is described in detail below in connection with the Figures for purposes of illustration, only. The invention is defined in the appended claims. Terminology used throughout the specification and claims herein are given their ordinary meanings, unless a more specific definition appears herein.

%, percent and like terminology means weight percent unless otherwise specifically indicated.

In general, the process of this invention can be applied to the dehydrogenation of a wide variety of organic compounds suitable as dehydrogenation reactants. Such compounds normally will contain from 2 to 20 carbon atoms, at least one

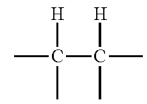

grouping, a boiling point below about 350° C., and may contain other elements, in addition to carbon and hydrogen, such as oxygen, halogens, nitrogen and sulfur. Preferred are compounds having 2 to 12 carbon atoms, and especially preferred, are compounds of 3 to 8 carbon atoms. Hydrocarbons of the above described carbon content form a preferred group.

Among the types of organic compounds which may be dehydrogenated by means of the process of this invention are nitriles, amines, alkyl halides, ethers, esters, aldehydes, ketones, alcohols, acids, alkyl aromatic compounds, alkyl heterocyclic compounds, alkenes, and the like. Illustration of dehydrogenation includes propionitrile to acrylonitrile; propionaldehyde to acrolein; ethyl chloride to vinyl chloride; methyl isobutyrate to methyl methacrylate; 2 or 3 chlorobutane-1 or 2,3-dichlorobutane to chloroprene; ethyl pyridine to vinyl pyridine; ethylbenzene to styrene; isopropylbenzene to alpha-methyl styrene; ethylchlorohexane to styrene; ethyl benzene to styrene; cyclohexane to benzene; methylbutene to isoprene; cyclopentane to cyclopentene and cyclopentadiene-1,3; n-octane to ethyl benzene and ortho-xylene; monomethylheptanes to xylenes; ethyl acetate to vinyl acetate; 2,4,4-trimethylpentene to xylenes; and the like.

More typically, the invention is applied to the manufacture of butadiene.

Unless otherwise indicated, "butadiene" or "BD" refers to 1,3 butadiene or mixtures comprising 1,3 butadiene.

Ethylene dimerized to n-butene is one preferred raw material source for oxidative dehydrogenation according to the invention. Ethylene may be dimerized into n-butenes by a variety of catalytic processes. One suitable method is to utilize a homogeneous catalyst system which includes a nickel compound such as nickel phosphine oxide and an alkyl aluminum co-catalyst such as ethyl aluminum dichloride. Such processes produce predominantly 2-butenes. See, for example, U.S. Pat. No. 5,162,595 to Wu, the disclosure of which is incorporated by reference.

Alternatively, ethylene is dimerized into n-butenes suitable for use in connection with the present invention through the use of a homogeneous catalyst system which includes an organometallic titanium catalyst. In general, such processes include a titanium organometallic complex with at least one alkoxide ligand and an alkyl aluminum co-catalyst to produce predominantly 1-butene as is seen, for example, in United States Patent Application Publication No. US 2011/0288308 of Grasset et al., noted above, the disclosure of which is incorporated herein by reference. One suitable catalytic system includes titanium tetrabutoxide and triethyl aluminum. Titanium-based dimerization processes may be relatively selective, such as the Alphabutol® process and are reported to reduce fractionation costs when 1-butene of relatively high purity is required:

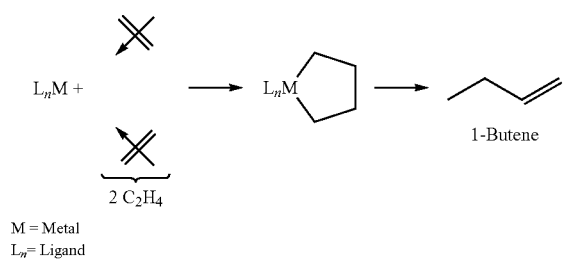

M = Metal
$L_n$ = Ligand

Another preferred source of raw material in some cases includes C4 Raffinate 2 and C4 Raffinate 3 streams. "Raffinate" refers to C4 streams wherein the butadiene has been removed by extraction as is well-known in the art. C4 Raffinate 2 refers to such streams where the isobutylene has also been removed, typically by reaction with methanol to make MTBE. C4 Raffinate 3 is produced from a C4 Raffinate 2 stream by removing the 1-butene. C4 Raffinate 2 and C4 Raffinate 3 are mixtures of butenes and butane as is seen in Table 1.

TABLE 1

Typical Compositions For C4 Raffinate 2 and C4 Raffinate 3 Streams, Per Cent by weight

| Components | C4 Raffinate 2 | C4 Raffinate 3 |
|---|---|---|
| Propylene | 0-1 | |
| Propadiene | 0-1 | |
| Isobutane | 1-7.5 | |
| Isobutylene (Isobutene) | 1-5 | |
| 1-Butene | 2.5-65 | 0.2 |
| 1,3-Butadiene | 0.1-0.5 | |
| Butane | 10-39 | 55.2 |
| Butene-2 (Isomer Mix) | 11-55 | 45.2 |

The hydrocarbon reactant butene(s) are added together with a hydrocarbon moderator gas, butane in such embodiments by using raffinate as feed.

"Moderator gas" and like terminology refers to gas which is substantially inert under conditions in the reactor, preferably undergoing conversion in the reactor of less than 10%; more preferably less than 5% and still more preferably less than 1% or 2%. Suitable moderator gasses generally include alkanes such as methane, ethane, propane, butane, pentane and hexane.

In a typical process, the reaction mixture comprises butenes, oxygen in an amount of from about 0.4 moles to about 0.8 moles, more typically from slightly in excess of 0.5 moles up to about 0.65 moles of oxygen for each mole of butene in the butene rich hydrocarbonaceous feed. Superheated steam in effective amounts in a molar ratio steam:butenes of from about 0.5:1 up to from 12:1 or about 16:1 or even 20:1 may be used depending upon reactor configuration. For relatively low steam/hydrocarbon ratios a preferred arrangement is shown in copending application 61/774,309 "Multi-Stage Oxidative Dehydrogenation Process with Inter-stage Cooling". Care should be exercised to avoid the flammable regions of the reaction mixture composition under reaction conditions, especially at low levels of inerts as is discussed hereinafter. With some reactor configurations the molar ratio of steam to butenes generally ranges from about 9:1 and to about 16:1. Subsequent to reaction, the reaction product mixture is cooled and compressed and butadiene separated by oil absorption and subsequent fractionation. Typically, these processes produce crude butadiene at a purity ranging from about 50 to about 70%, more typically from about 55 to about 65%, which is passed onward in the plant for further processing using known technologies.

Hydrocarbon levels in the feed, exclusive of butenes or other dehydrogenation reactants, are adjusted in some cases to levels such that the molar ratio of hydrocarbon moderator gas to oxygen is generally from 8:1 to 0.5:1; typically from 4:1 to 1:1 and preferably from 3:1 to 1.5:1. The hydrocarbon moderator gas advantageously comprises ingredients selected from methane, ethane, propane, butane, pentane and hexane. Preferably, the hydrocarbon moderator gas is added as natural gas having a methane content of at least 75%.

In accordance with the invention the oxygen/nitrogen molar ratio of the feed stream in preferred cases is greater than 0.27, with pure oxygen being used in some cases which provides a very high oxygen/nitrogen ratio, up to 200 and more. In various typical embodiments, the oxygen/nitrogen molar ratio in the feed to the reactor is at least 0.3, at least 0.5, at least 1, at least 2, at least 5, at least 10, at least 15 or at least 20.

An oxidative dehydrogenation process for making butadiene of this invention includes providing a butene rich hydrocarbonaceous feed, vaporizing and superheating said hydrocarbonaceous butene rich feed, mixing said hydrocarbonaceous butene rich feed with superheated steam and an oxygen containing gas to form a reactor feed stream, reacting said reactor feed stream over a ferritic oxide catalyst, thereby forming a butadiene enriched product stream. The butadiene enriched product stream leaving the reactor is cooled through a quench column, in which heat is removed from the butadiene enriched product stream and steam content thereof condensed. After being compressed, the butadiene enriched product stream is directed to a scrubber, and ultimately, a C4 absorber. the C4 species contained in the butadiene enriched product stream are removed in the C4 absorber column by absorption leaving nitrogen, hydrogen, and lighter hydrocarbon species to be removed in a gaseous overhead stream Details appear in Welch et al., *Butadiene via oxidative dehydrogenation*, Hydrocarbon Processing, November 1978, pp. 131-136; as well as U.S. Pat. No. 4,083,844 to Purdy, the disclosures of which are incorporated herein by reference.

The present invention relates, in part, in the use of a hydrocarbon moderator gas which acts as a heat sink instead of nitrogen when oxygen enriched feed mixtures are used. It will be appreciated from Table 2, that at temperatures of interest that methane and steam both have heat capacities on a weight basis much higher than nitrogen and are advantageously employed in connection with the present invention.

TABLE 2

Heat Capacity of Stream Components

| Temperature °F. | Pressure psia | Vapor Heat Capacity CP $N_2$ Btu/lb-°F. | Vapor Heat Capacity CP $CH_4$ Btu/lb-°F. | Vapor Heat Capacity CP Steam Btu/lb-°F. |
|---|---|---|---|---|
| 650 | 34.7 | 0.258 | 0.796 | 0.486 |
| 703 | 34.7 | 0.260 | 0.821 | 0.490 |
| 739 | 34.7 | 0.260 | 0.838 | 0.493 |

Other alkanes such as ethane, propane, butane, pentane and hexane have heat capacities somewhat lower than methane, but higher than steam at temperatures of interest and may be substituted for methane or mixed with natural gas depending upon availability. Table 3 provides heat capacity data for selected gasses at 800° F. and 1 atmosphere absolute pressure.

TABLE 3

Heat Capacity for Selected gasses at 800° F.

| Gas | Heat Capacity, $C_p$, BTU/Lb °F. |
|---|---|
| Steam | 0.5 |
| Methane | 0.87 |
| Ethane | 0.79 |
| Propane | 0.77 |
| n-Butane | 0.76 |

Table 4 provides the substitution, W/W (weight basis) for replacing nitrogen with steam and/or steam or nitrogen with methane and maintaining a given heat capacity in the feed. It is seen that less methane is needed than either nitrogen or steam to maintain a given heat capacity for the feed to an adiabatic reaction zone in order to moderate temperature increases. That is, methane provides superior heat sink properties to moderate temperature increases in the reaction zone than either nitrogen or steam. In other words, the relatively high heat capacity of the moderator gas promotes sensible heat flux for heat removal in the system to prevent overheating. Flow rates for various streams in the production process are accordingly reduced, along with equipments size and capital costs as is appreciated form the discussion which follows.

TABLE 4

Heat Sink Substitutions at different Temperatures

| Reactor Feed @ 650° F. | |
|---|---|
| 0.530 | LB of Steam/LB of $N_2$ removed |
| 0.324 | LB of $CH_4$/LB of $N_2$ removed |
| 0.611 | LB of $CH_4$/LB of Steam removed |
| Reactor Feed @ 703° F. | |
| 0.528 | LB of Steam/LB of $N_2$ removed |
| 0.316 | LB of $CH_4$/LB of $N_2$ removed |
| 0.597 | LB of $CH_4$/LB of Steam removed |
| Reactor Feed @ 750° F. | |
| 0.527 | LB of Steam/LB of $N_2$ removed |
| 0.309 | LB of $CH_4$/LB of $N_2$ removed |
| 0.586 | LB of $CH_4$/LB of Steam removed |

Referring to FIG. 1, there is shown schematically an air-fed butadiene production system 10 of the class described herein for producing 100 units/hr of crude butadiene. "Units" refers to weight units in the discussion herein and on the Figures.

System 10 includes a reaction section 12, quenching and compression sections indicated at 14, as well as scrubbing and absorption units indicated at 16 and degassing and stripping apparatus provided at 18.

In the process, air is fed to reaction section 12 along with n-butene and steam via lines 20, 22, 24. The effluent is forwarded to quenching and compression 14 via line 26 and most of the water is recycled to the reaction system via line 28. After quenching and compression an output stream 30 is forwarded to scrubbing and absorption 16. Butadiene product is absorbed in an absorbent tower at 16 and liquid effluent is passed via line 32 to degassing and stripping at 18, while overhead gas is provided to heat recovery via line 34.

From degassing and stripping at 18, off-gas is partially recycled via line 36 to quenching and compression at 14. The degassed fat absorber oil containing butadiene is fed forward via line 40 for extraction and further purification. Clean absorber oil is recycled to section 16.

Figure 2:
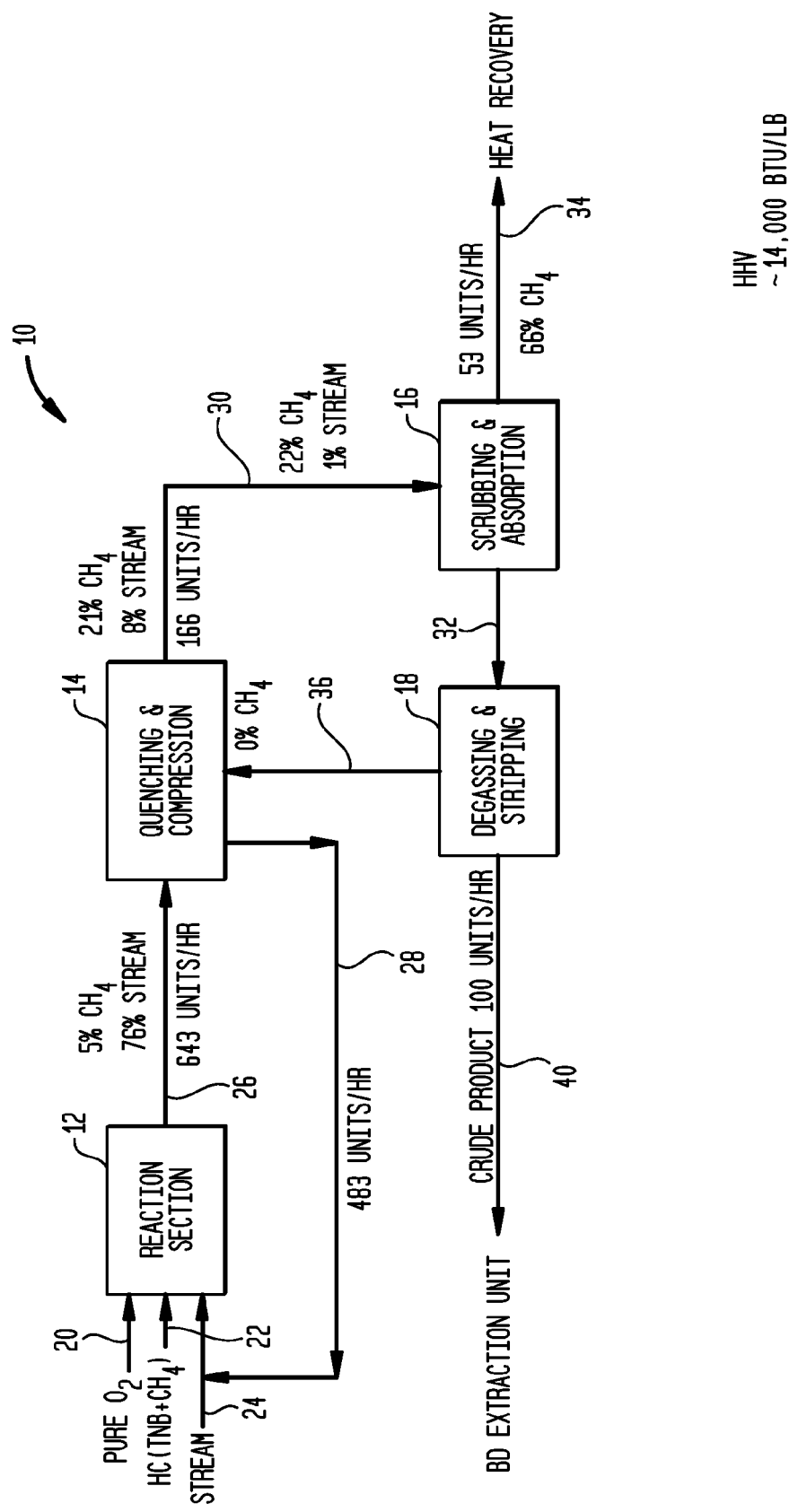
FIG. 2 is a schematic diagram illustrating an oxidative dehydrogenation system to make butadiene from butene with pure oxygen as the oxygen source and methane as a moderator gas in the feed in accordance with the invention.
Figure 4:
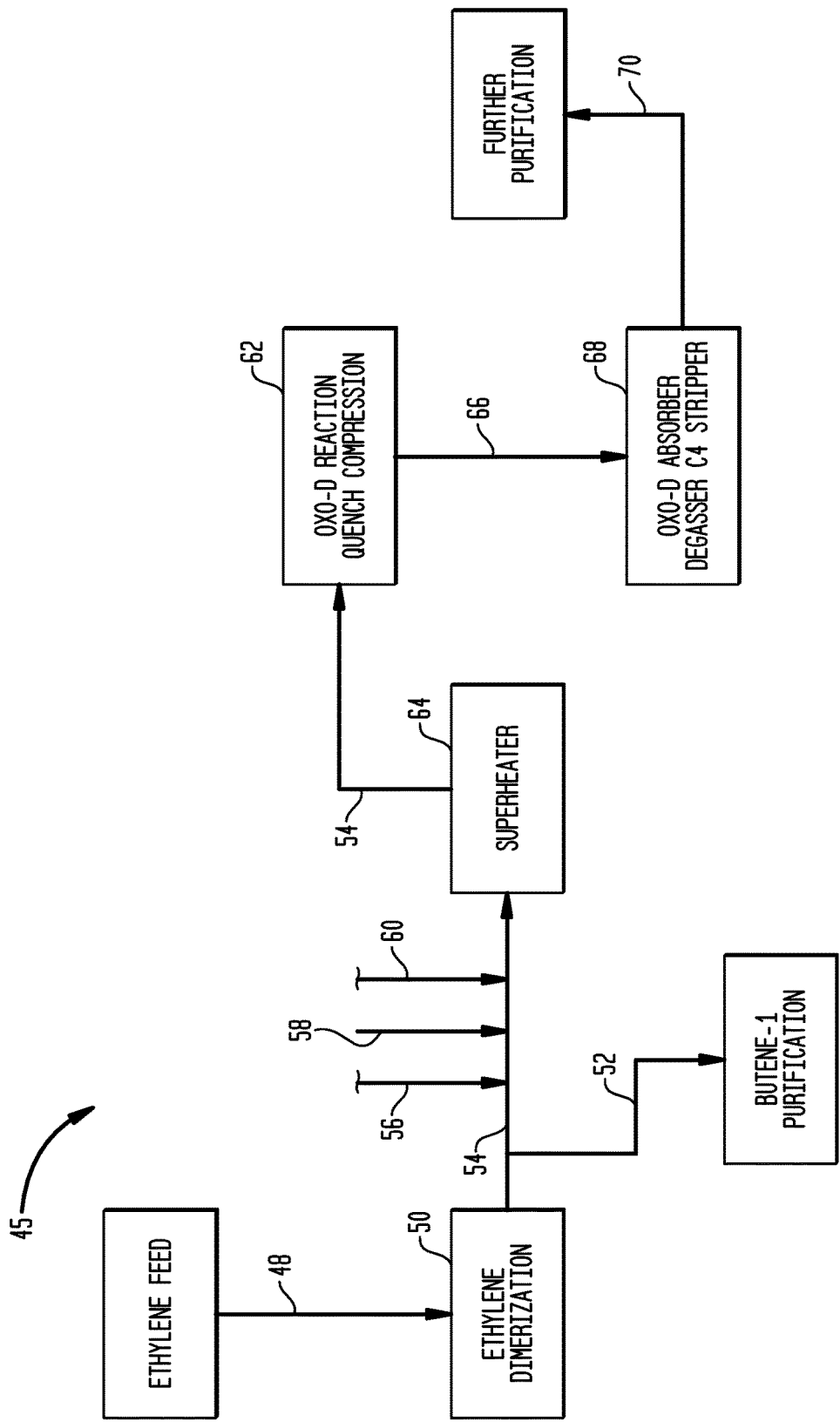
FIG. 4 is a flow diagram illustrating an oxidative dehydrogenation system of the invention to make butene and butadiene based on ethylene as the raw material using the oxidative dehydrogenation processes illustrated schematically in FIGS. 2, 3.

FIG. 2 illustrates a process of the invention for producing 100 units/hr of crude butadiene product by way of a similar process to that of FIG. 1, except that instead of air feed to the oxidative dehydrogenation unit, oxygen and methane and n-butene are provided via lines 20, 22 wherein the butene is optionally provided by stream 54 from reactor 50 of FIG. 4 by way of superheater 64.

FIG. 1 air fed process feed stream components and FIG. 2 methane and oxygen enriched feed stream components are compared in Table 5.

TABLE 5

Reactor Feed

| Component | Air Fed Mole Percent | Air Fed Mass Percent | Ox/$CH_4$ Fed Mole Percent | Ox/$CH_4$ Fed Mass Percent |
|---|---|---|---|---|
| $N_2$ | 12% | 15.4% | — | — |
| $CH_4$ | — | — | 7.0% | 5.4% |
| Steam | 78.7% | 64.7% | 83.3% | 72.4% |

Figure 3:
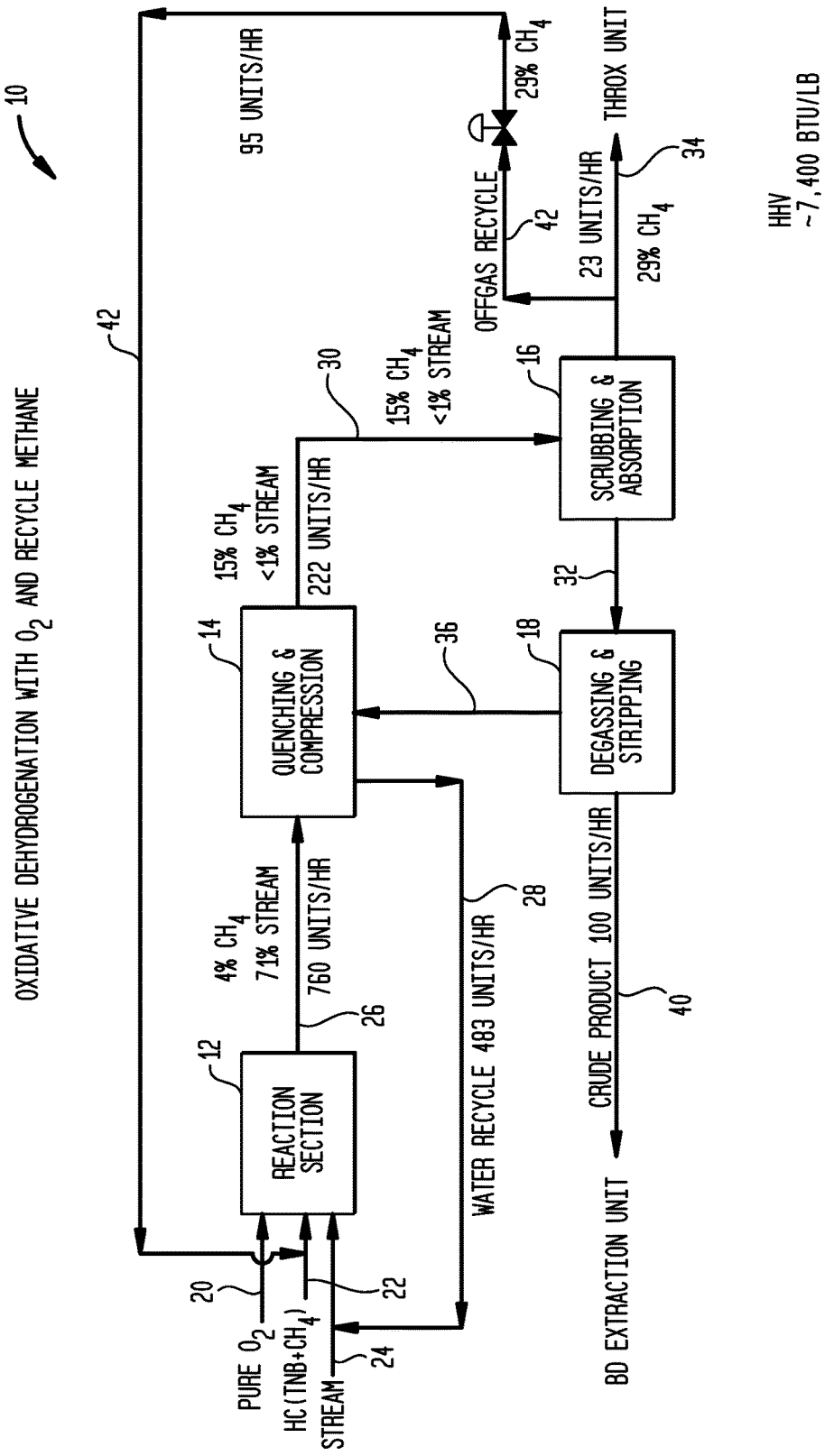
FIG. 3 is a schematic diagram illustrating an oxidative dehydrogenation system to make butadiene from butene with pure oxygen as the oxygen source and methane as a moderator gas in the feed with recycle of moderator gas to the reactor in accordance with the invention.

Relative flow rates and various stream components are indicated on FIGS. 1, 2 and 3 for producing 100 units/hr of crude butadiene product.

It will be appreciated from FIGS. 1 and 2 that the use of a hydrocarbon moderator gas in the process of the invention greatly reduces the volumes that need to be processed in the purification and recycle sections of butadiene production. It is estimated that such stream volume reductions reduce capital costs by about 30% for the equipment shown. Processing costs are also reduced by similar levels. Moreover, it is seen that the off-gas provided for heat recovery has about 35 times more heat value than the 85% nitrogen offgas from an air-fed process. A still further advantage of the invention is that as one feeds less lbs of reactants and carrier gas through the reactor one may reduce pressure drop and pressure across the catalyst, which improves selectivity.

Among the differences between the invention and air-fed systems are that: (i) air compressors are eliminated; (ii) hydrocarbon gas injection into the reactor feed is required to supplement the "heat sink" effect lost by the removal of nitrogen, and to shift the hydrocarbon/oxygen mixture outside of the flammability region. The amount of moderator gas injected preferably is such to eliminate any need for additional steam, so there is no increase in the steam requirements for the unit, or the size of steam vaporizers.

Recycling a relatively large proportion of the moderator gas is especially preferred in some embodiments. Referring to FIG. 3, there is shown a production system which illustrates a process of the invention for producing 100 units/hr of crude butadiene product by way of a similar process to that of FIG. 2, except that part of the offgas is separated and recycled to reaction section 12 via line 42, as shown. Depending on the composition recycled to the reactor, it may be desirable to adjust the oxygen or other feed to the reactor. The embodiment shown in FIG. 3 greatly reduces the amount of offgas that must be thermally oxidized as compared to the embodiment of FIG. 2, while maintaining a relatively high heating value of offgas as compared with the air-fed process of FIG. 1.

A comparison of system characteristics appears in Table 6, below:

TABLE 6

Comparison of System Performance, Air-Fed vs. $O_2$/Moderator Gas

| System of | Crude Product Stream | Heat Recovery Streams | Absorber and Scrubber Feed |
|---|---|---|---|
| FIG. 1 Air-Fed | 100 units/hr | 131 units/hr HHV ~400 BTU/lb | 244 units/hr |
| FIG. 2 $O_2$/Moderator Gas | 100 units/hr | 53 units/hr HHYV ~14,000 BTU/lb | 166 units/hr |
| FIG. 3 $O_2$/Moderator Gas with Gas Recycle | 100 units/hr | 23 units/hr HHV ~7,400 BTU/lb | 222 units/hr |

As it is appreciated from Table 6, offgas from the process is greatly reduced with the $O_2$/moderator gas system and the offgas stream has a much higher heating value so as to be suitable for boiler feed. Additional advantages include lower volumes of gas that require compression, scrubbing and absorption for a given level of production, especially in the embodiment of FIG. 2. Moreover, the $O_2$/moderator gas system eliminated nitrogen recycle which is costly in terms of both operating expense and capital expense.

One preferred embodiment of the present invention is a co-production system 45 shown schematically in FIG. 4. Ethylene is provided to a homogeneous reactor 50 containing a titanium/aluminum homogeneous catalyst via line 48 wherein butene-1 is produced from the ethylene. The butene-1 is provided to a butene-rich product stream 52 as well as a butene-1 rich feed stream 54.

Stream 52 is purified and butene-1 (>99%) is recovered therefrom, while stream 54 is mixed with steam 56, a moderator gas 58 and an oxygen rich gas 60 and provided to an oxidative dehydrogenation unit as part of a reaction/quench/compression section 62 after superheating in a superheater 64. Output 66 is enriched in butadiene and contains butene-1.

Stream 66 is fed to a product recovery system including an absorber, degasser and stripper units indicated at 68 and a crude butadiene stream 70 is recovered as described in connection with FIGS. 1-3. Stream 70 is typically 50-60% by weight butadiene and is further purified by conventional means in order to provide butadiene of greater than 99% purity, while other C4's are recycled or otherwise recovered.

A particularly preferred moderator gas for use in connection with the invention is methane, which may be provided in the form of natural gas. While natural gas compositions vary somewhat, natural gas may have the compositions similar to compositions I or II set forth in U.S. Pat. No. 5,653,916, which have varying levels of methane, nitrogen and other hydrocarbons.

| Natural Gas with composition I: | | Natural Gas with composition II: | |
|---|---|---|---|
| Component | Percent by volume | Component | Percent by volume |
| $CH_4$ | 94.4% | $CH_4$ | 81.8% |
| $C_2H_6$ | 3.0% | $C_2H_6$ | 2.7% |
| $C_3H_8$ | 0.5% | $C_3H_8$ | 0.4% |
| $C_4H_{10}$ | 0.2% | $C_4H_{10}$ | 0.1% |
| $C_5H_{10}$ | 0.2% | $C_5H_{10}$ | 0.1% |
| $CO_2$ | 0.2% | $CO_2$ | 0.9% |
| $N_2$ | 1.5% | $N_2$ | 14% |

In preferred embodiments, the oxygen/nitrogen ratio of the oxygen source is increased over that of air by providing to the feed purified oxygen which may be prepared from air by a variety of means including cryogenic distillation, pressure swing adsorption, or membrane separation as will be appreciated by one of skill in the art.

Figure 5:
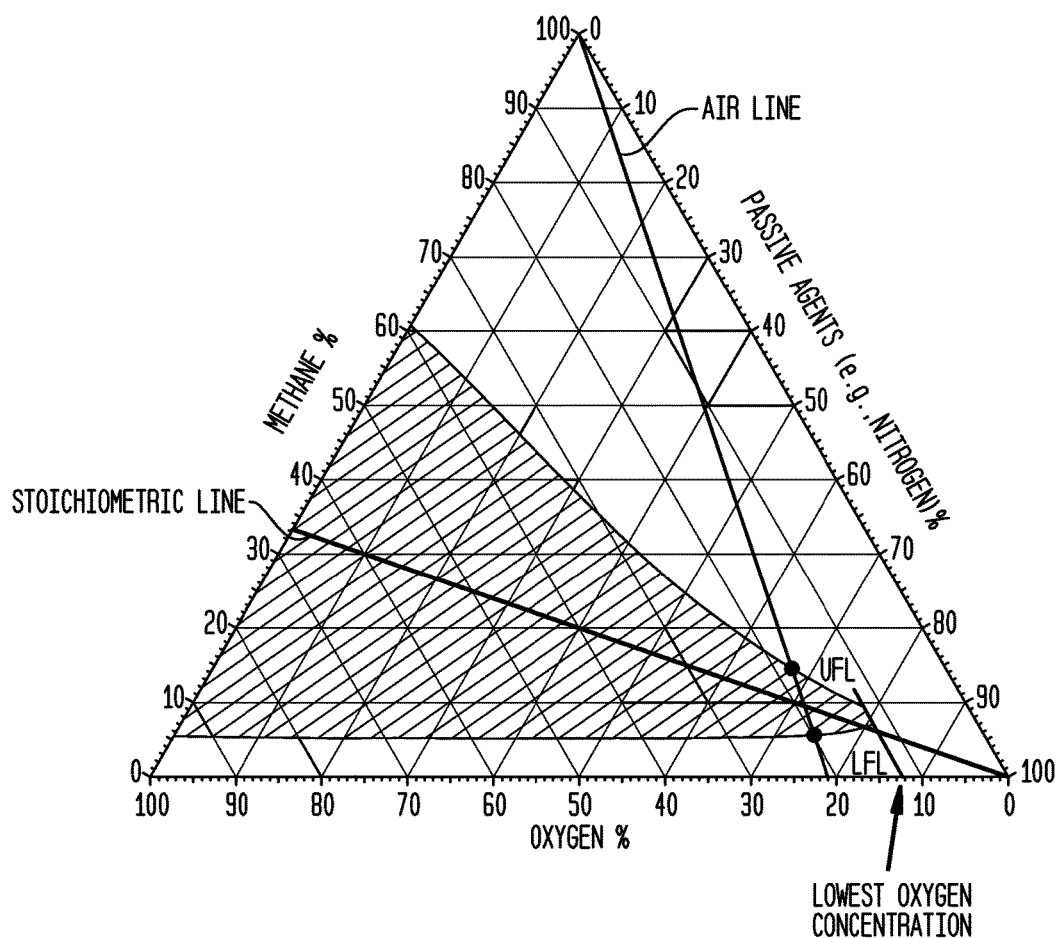
FIG. 5 is a ternary flammability diagram for methane/oxygen/inert gas mixtures sourced from http://cfbt-us.com/wordpress/?p=421 (2013 Attributed to GexCon).

Referring to FIG. 5, there is shown a ternary diagram illustrating the flammability region (shaded) of mixtures of methane/oxygen/and inerts such as nitrogen or steam on a mol % basis for a predetermined temperature and pressure. One of skill in the art will appreciate that the flammability region will vary depending on temperature, pressure, and composition of flammables/hydrocarbons in the reactor. It is seen in the diagram that at low levels of inerts especially, the flammability region for hydrocarbons is much expanded, as toward the left of the diagram. In operating the process of the present invention, it is much preferred to control the mixture composition, temperatures and pressures to operate outside of the flammability region of the reaction mixtures. A preferred method of operation is to add the oxygen to the steam and then mix the hydrocarbons. This avoids the "nose" of the flammability triangle and stays on the "fuel rich" side of the envelope.

For particular reaction compositions and conditions, flammability limits can be determined empirically or calculated from component data based on Le Chatelier's mixing rule, for example, for the lower flammability limit, LFL:

$$LFL_{Mix} = \frac{100}{C_1/LFL_1 + C_2/LFL_2 + \cdots + C_i/LFL_i}$$

The invention thus includes in its various aspects, a first embodiment directed to a method of oxidatively dehydrogenating a dehydrogenation reactant comprising: (a) providing a gaseous feed steam to a catalytic reactor, the feed stream comprising a dehydrogenation reactant, oxygen, superheated steam and a hydrocarbon moderator gas, wherein the molar ratio of hydrocarbon moderator gas to oxygen in the feed stream is from 50:1 to 0.5:1; (b) oxidatively dehydrogenating the dehydrogenation reactant in the reactor to generate an effluent product stream enriched in a dehydrogenated product derived from said dehydrogenation reactant; and (c) recovering said dehydrogenated product from the effluent product stream. Features of the first embodiment include in additional embodiments any of the following numbered embodiments which include the features of the first embodiment and in combination as indicated: (2) wherein the molar ratio of hydrocarbon moderator gas to oxygen in the feed stream is selected from any of the following ratios: 20:1 to 0.5:1; 15:1 to 0.5:1; 8:1 to 0.5:1 or 4:1 to 1:1; (3) wherein the molar ratio of hydrocarbon moderator gas to oxygen in the feed stream is from 3:1 to 1.5:1; (4) wherein the feed stream optionally comprises nitrogen and the molar ratio of oxygen:nitrogen in the feed stream is at least 0.5; (5) embodiment 4, wherein the molar ratio of oxygen:nitrogen in the feed stream is at least 2; (6) embodiment 5, wherein the molar ratio of oxygen:nitrogen in the feed stream is at least 10; (7) embodiment 6, wherein the molar ratio of oxygen:nitrogen in the feed stream is at least 20; (8) any of the foregoing embodiments, wherein the molar ratio of oxygen to dehydrogenation reactant in the feed stream is from 0.1:1 to 0.85:1 or from 0.4:1 to 0.8:1 or from 0.2:1 to 0.4:1; (9) embodiment 8, wherein the molar ratio of steam to dehydrogenation reactant in the feed stream is from 0.5:1 to 20:1 or from 0.5:1 to 16:1; (10) any of the foregoing embodiments, wherein the catalytic reactor has disposed therein a ferrite catalyst; (11) any of the foregoing embodiments, further comprising recovering from the effluent product stream a heat recovery stream having a heating value of greater than 2,500 Btu/lb; (12) embodiment 11, further comprising recovering from the effluent product stream a heat recovery stream having a heating value of greater than 5,000 Btu/lb; (13) embodiment 12, further comprising recovering from the effluent product stream a heat recovery stream having a heating value of greater than 10,000 Btu/lb; (14) any of the foregoing embodiments, wherein said moderator gas comprises an alkane; (15) embodiment 14, wherein said moderator gas comprises methane, ethane, propane, butane, pentane or hexane; (16) embodiment 15, wherein said moderator gas comprises methane; (17) any of the foregoing embodiments, wherein natural gas is provided to the feed stream; (18) any one of the foregoing embodiments, wherein said dehydrogenation reactant comprises n-butenes and said dehydrogenated product comprises butadiene; (19) any one of the foregoing embodiments, wherein said dehydrogenation reactant comprises butenes and said dehydrogenated product comprises butadiene and the first gaseous feed stream comprises butenes and butane; (20) embodiment 19, wherein said gaseous feed stream comprises C4 Raffinate 2 or C4 Raffinate 3.

Embodiment 21 is a method according to any of embodiments 1-20, further comprising: (d) recovering moderator gas from the from the effluent product stream and; and (e) recycling moderator gas recovered from the effluent product stream to the reactor. Embodiments 22-28 include all of the features of embodiment 21, and are further characterized in that: (22) at least 25% by weight of the moderator gas in the effluent product stream is recovered and recycled to the reactor; (23) at least 50% by weight of the moderator gas in the effluent product stream is recovered and recycled to the reactor; (24) at least 75% by weight of the moderator gas in the effluent product stream is recovered and recycled to the reactor; (25) at least 85% by weight of the moderator gas in the effluent product stream is recovered and recycled to the reactor; (26) at least 90% by weight of the moderator gas in the effluent product stream is recovered and recycled to the reactor; (27) from 50% by weight up to 97.5% by weight of the moderator gas in the effluent product stream is recovered and recycled to the reactor.

Embodiment (28) is a method according to any of embodiments 1-27, wherein the gaseous feed stream to the reactor is prepared by first mixing oxygen and steam and then adding hydrocarbon gas to the mixture so as to avoid flammability limits during processing.

Still another aspect of the invention is embodiment 29, directed to a method of producing butadiene from an ethylene raw material feed comprising: (a) providing ethylene to a homogeneous reaction medium housed in a dimerization reactor; (b) dimerizing ethylene to n-butene in the homogeneous reaction medium to provide a hydrocarbonaceous n-butene rich feed; (c) mixing said hydrocarbonaceous butene rich feed with steam, oxygen and a hydrocarbon moderator gas to form an oxidative dehydrogenation reactor feed stream and superheating said oxidative dehydrogenation reactor feed stream to a temperature of at least 204° C. (400° F.), wherein the molar ratio of hydrocarbon moderator gas to oxygen in the feed stream is from 8:1 to 0.5:1; (d) feeding the an oxidative dehydrogenation reactor feed stream to an oxidative dehydrogenation reactor; (e) oxidatively dehydrogenating the n-butene reactant in the oxidative dehydrogenation reactor to generate an effluent product stream enriched in butadiene derived from said n-butene; and (f) recovering said butadiene from the effluent product stream. The method of embodiment 29 may further include any of the features as is noted below in connection with embodiments 30-49: (30) wherein the molar ratio of hydrocarbon moderator gas to oxygen in the oxidative dehydrogenation reactor feed stream is from 4:1 to 1:1; (31) wherein the molar ratio of hydrocarbon moderator gas to oxygen in the oxidative dehydrogenation reactor feed stream is from 3:1 to 1.5:1; (32) wherein the oxidative dehydrogenation reactor feed stream optionally comprises nitrogen and the molar ratio of oxygen:nitrogen in the oxidative dehydrogenation reactor feed stream is at least 0.5; (33) wherein the molar ratio of oxygen:nitrogen in the oxidative dehydrogenation reactor feed stream is at least 2; (34) wherein the molar ratio of oxygen:nitrogen in the oxidative dehydrogenation reactor feed stream is at least 10; (35) wherein the molar ratio of oxygen:nitrogen in the oxidative dehydrogenation reactor feed stream is at least 20; (36) further comprising recovering from the effluent product stream a heat recovery stream having a heating value of greater than 2,500 Btu/lb; (37) the method of embodiment 36, further comprising recovering from the effluent product stream a heat recovery stream having a heating value of greater than 5,000 Btu/lb; (38) the method of embodiment 37, further comprising recovering from the effluent product stream a heat recovery stream having a heating value of greater than 10,000 Btu/lb; (39) wherein said moderator gas comprises an alkane; (40) wherein said moderator gas comprises methane, ethane, propane, butane, pentane or hexane; (41) wherein said moderator gas comprises methane; (42) wherein natural gas is provided to the oxidative dehydrogenation reactor feed stream; (43) wherein the homogeneous reaction medium in the dimerization reactor comprises a homogeneous catalyst comprising a nickel compound and an alkyl aluminum co-catalyst; (44) wherein the homogeneous catalyst comprises a nickel phosphine oxide and ethyl aluminum dichloride; (45) wherein the n-butene in the oxidative dehydrogenation reaction feed stream are predominantly 2-butenes; (46) wherein the homogeneous reaction medium in the dimerization reactor comprises a homogeneous titanium/aluminum catalyst; (47) wherein the homogeneous titanium/aluminum catalyst comprises a titanium organometallic complex with at least one alkoxide ligand and an alkyl aluminum co-catalyst; (48) wherein the homogeneous titanium/aluminum catalyst comprises titanium tetrabutoxide and triethyl aluminum; and (49) wherein the butene in the oxidative dehydrogenation reactor feed stream is predominantly 1-butene.

Still yet another aspect of the invention is embodiment 50, directed to a method of co-producing butene-1 and butadiene from an ethylene raw material feed comprising: (a)

providing ethylene to a homogeneous reaction medium including a homogeneous titanium/aluminum catalyst housed in a dimerization reactor; (b) dimerizing ethylene predominantly to butene-1 in the homogeneous reaction medium to provide (i) a hydrocarbonaceous butene-1 rich feed and (ii) a butene-1 rich product stream; (c) withdrawing and purifying the butene-1 rich product stream and recovering butene-1 therefrom; (d) mixing said hydrocarbonaceous butene rich feed with steam, oxygen and a hydrocarbon moderator gas to form an oxidative dehydrogenation reactor feed stream and superheating said oxidative dehydrogenation reactor feed stream to a temperature of at least 204° C. (400° F.), wherein the molar ratio of hydrocarbon moderator gas to oxygen in the feed stream is from 8:1 to 0.5:1; (e) feeding the an oxidative dehydrogenation reactor feed stream feed stream to an oxidative dehydrogenation reactor; (f) oxidatively dehydrogenating the n-butene in oxidative dehydrogenation reactor to generate an effluent product stream enriched in butadiene derived from said n-butene; and (g) recovering said butadiene from the effluent product stream. Additional features of embodiment 50 are included in embodiments (51) wherein the homogeneous titanium/aluminum catalyst comprises a titanium organometallic complex with at least one alkoxide ligand and an alkyl aluminum co-catalyst; and (52) wherein the homogeneous titanium/aluminum catalyst comprises titanium tetrabutoxide and triethyl aluminum.

Embodiment 53 is directed to the method according to any of embodiments 29-52, further comprising: recovering moderator gas from the from the effluent product stream and; and recycling moderator gas recovered from the effluent product stream to the reactor. Embodiment 54 includes the features of embodiment 53 and further encompasses wherein at least 25% by weight of the moderator gas in the effluent product stream is recovered and recycled to the reactor; while embodiments 55-59 includes the features of embodiment 53 and further include the following additional parameters: (55) wherein at least 50% by weight of the moderator gas in the effluent product stream is recovered and recycled to the reactor; (56) wherein at least 75% by weight of the moderator gas in the effluent product stream is recovered and recycled to the reactor; (57) wherein at least 85% by weight of the moderator gas in the effluent product stream is recovered and recycled to the reactor; (58) wherein at least 90% by weight of the moderator gas in the effluent product stream is recovered and recycled to the reactor; (59) wherein from 50% by weight up to 97.5% by weight of the moderator gas in the effluent product stream is recovered and recycled to the reactor.

In any method according to the invention, the gaseous feed stream to the reactor may be prepared by first mixing oxygen and steam and then adding hydrocarbon gas to the mixture so as to avoid flammability limits during processing.

When moderator gas is used in place of steam, which may be in connection with any of the foregoing embodiments, moderator gas:reactant hydrocarbon molar ratios of anywhere from 3 to 12 are typical, with moderator gas:oxygen molar ratios of from 8:1 to 45:1 being typical. Following are exemplary ratios which may be used with or without air in the feed and with or without purified oxygen in the feed in connection with any of the foregoing embodiments:

TABLE 7

| Steam Replacement Molar Ratios | | |
|---|---|---|
| Steam to HC | Methane to HC | Methane to Oxygen |
| 3 | 12 | 41.9 |
| 5 | 10 | 34.9 |
| 7 | 8 | 27.9 |
| 9 | 6 | 20.9 |
| 12 | 3 | 10.48 |

Moderator gas:oxygen molar ratios of from 10:1 to 30:1 are preferred in some cases.

While the invention has been described in detail, modifications within the spirit and scope of the invention will be readily apparent to those of skill in the art. In view of the foregoing discussion, relevant knowledge in the art and references, including co-pending applications, discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A method of oxidatively dehydrogenating a dehydrogenation reactant comprising:
    (a) providing a gaseous feed stream to a catalytic reactor, the feed stream comprising a dehydrogenation reactant, oxygen, superheated steam and a hydrocarbon moderator gas,
        wherein hydrocarbon moderator gas is added to the dehydrogenation reactant to adjust the amount of moderator gas in the gaseous feed stream; and
        wherein the molar ratio of hydrocarbon moderator gas to oxygen in the feed stream is from 50:1 to 0.5:1;
    (b) oxidatively dehydrogenating the dehydrogenation reactant in the reactor to generate an effluent product stream enriched in a dehydrogenated product derived from said dehydrogenation reactant; and
    (c) recovering said dehydrogenated product from the effluent product stream.

2. The method according to claim 1, wherein the molar ratio of hydrocarbon moderator gas to oxygen in the feed stream is from 8:1 to 0.5:1.

3. The method according to claim 1, wherein the molar ratio of hydrocarbon moderator gas to oxygen in the feed stream is from 3:1 to 1.5:1.

4. The method according to claim 1, wherein the feed stream optionally comprises nitrogen and the molar ratio of oxygen:nitrogen in the feed stream is at least 0.5.

5. The method according to claim 2, wherein the molar ratio of oxygen:nitrogen in the feed stream is at least 2.

6. The method according to claim 1, wherein the molar ratio of oxygen to dehydrogenation reactant in the feed stream is from 0.2:1 to 0.4:1.

7. The method according to claim 1, wherein the molar ratio of oxygen to dehydrogenation reactant in the feed stream is from 0.4:1 to 0.8:1.

8. The method according to claim 1, wherein the catalytic reactor has disposed therein a ferrite catalyst.

9. The method according to claim 1, further comprising recovering from the effluent product stream a heat recovery stream having a heating value of greater than 5,000 Btu/lb.

10. The method according to claim 1, wherein said moderator gas comprises an alkane.

11. The method according to claim 10, wherein said moderator gas comprises methane, ethane, propane, butane, pentane or hexane.

12. The method according to claim 11, wherein said moderator gas comprises methane.

13. The method according to claim 1, wherein said dehydrogenation reactant comprises n-butenes and said dehydrogenated product comprises butadiene.

14. The method according to claim 1, further comprising:
(d) recovering moderator gas from the from the effluent product stream; and
(e) recycling moderator gas recovered from the effluent product stream to the reactor.

15. The method according to claim 14, wherein from 50% by weight up to 97.5% by weight of the moderator gas in the effluent product stream is recovered and recycled to the reactor.

16. A method of producing butadiene from an ethylene raw material feed comprising:
(a) providing ethylene to a homogeneous reaction medium housed in a dimerization reactor;
(b) dimerizing ethylene to n-butene in the homogeneous reaction medium to provide a hydrocarbonaceous n-butene rich feed;
(c) mixing said hydrocarbonaceous butene rich feed with steam, oxygen and a hydrocarbon moderator gas to form an oxidative dehydrogenation reactor feed stream and superheating said oxidative dehydrogenation reactor feed stream to a temperature of at least 204° C. (400° F.), wherein the molar ratio of hydrocarbon moderator gas to oxygen in the feed stream is from 8:1 to 0.5:1;
(d) feeding the an oxidative dehydrogenation reactor feed stream to an oxidative dehydrogenation reactor;
(e) oxidatively dehydrogenating the n-butene reactant in the oxidative dehydrogenation reactor to generate an effluent product stream enriched in butadiene derived from said n-butene; and
(f) recovering said butadiene from the effluent product stream.

17. The method according to claim 16, wherein the homogeneous reaction medium in the dimerization reactor comprises a homogeneous catalyst comprising a nickel compound and an alkyl aluminum co-catalyst.

18. The method according to claim 17, wherein the homogeneous catalyst comprises a nickel phosphine oxide and ethyl aluminum dichloride.

19. The method according to claim 16, wherein the n-butene in the oxidative dehydrogenation reaction feed stream are predominantly 2-butenes.

20. A method of co-producing butene-1 and butadiene from an ethylene raw material feed comprising:
(a) providing ethylene to a homogeneous reaction medium including a homogeneous titanium/aluminum catalyst housed in a dimerization reactor;
(b) dimerizing ethylene predominantly to butene-1 in the homogeneous reaction medium to provide (i) a hydrocarbonaceous butene-1 rich feed and (ii) a butene-1 rich product stream;
(c) withdrawing and purifying the butene-1 rich product stream and recovering butene-1 therefrom;
(d) mixing said hydrocarbonaceous butene rich feed with steam, oxygen and a hydrocarbon moderator gas to form an oxidative dehydrogenation reactor feed stream and superheating said oxidative dehydrogenation reactor feed stream to a temperature of at least 204° C. (400° F.), wherein the molar ratio of hydrocarbon moderator gas to oxygen in the feed stream is from 8:1 to 0.5:1;
(e) feeding the an oxidative dehydrogenation reactor feed stream feed stream to an oxidative dehydrogenation reactor;
(f) oxidatively dehydrogenating the n-butene in oxidative dehydrogenation reactor to generate an effluent product stream enriched in butadiene derived from said n-butene; and
(g) recovering said butadiene from the effluent product stream.

21. The method according to claim 1, wherein natural gas is provided to the feed stream.

22. The method according to claim 1, wherein the hydrocarbon moderator gas:reactant hydrocarbon molar ratio is from 3 to 12 and the hydrocarbon moderator gas:oxygen molar ratio is from 8:1 to 45:1.

* * * * *